United States Patent [19]

Langston et al.

[11] 4,144,309
[45] Mar. 13, 1979

[54] DEVICE FOR DISPENSING MICROCIDE FORMED WHEN DEVICE IS IN ENVIRONMENT OF USE

[75] Inventors: Jimmy B. Langston, San Jose; Harold Leeper, Mountain View; Patrick S. Wong, Palo Alto, all of Calif.

[73] Assignee: Alza Corporation, Palo Alto, Calif.

[21] Appl. No.: 804,961

[22] Filed: Jun. 9, 1977

[51] Int. Cl.² .............................................. A61L 9/04
[52] U.S. Cl. ...................... 422/305; 43/125; 43/129; 239/43; 239/54; 239/60; 422/180; 422/306
[58] Field of Search .............. 21/108, 109, 53, 74 R, 21/58; 43/125, 129; 239/43, 54, 60

[56] References Cited
U.S. PATENT DOCUMENTS

| 1,080,716 | 12/1913 | Rand | 21/108 UX |
| 2,861,965 | 11/1958 | Roncoroni | 239/43 UX |
| 3,310,235 | 3/1967 | Zbinden | 239/43 X |
| 3,595,607 | 7/1971 | Gores | 21/74 R |
| 3,630,348 | 12/1971 | Benson et al. | 21/58 X |
| 3,688,985 | 9/1972 | Engel | 239/54 |
| 3,694,146 | 9/1972 | Roy et al. | 21/110 X |
| 3,719,751 | 3/1973 | Rauscher et al. | 21/58 X |
| 3,942,634 | 3/1976 | Gandi et al. | 21/58 X |
| 3,994,439 | 11/1976 | Van Breen et al. | 239/54 |
| 4,050,576 | 9/1977 | Williams et al. | 21/58 X |

FOREIGN PATENT DOCUMENTS

| 2088119 | 7/1972 | France | 239/54 |
| 2298952 | 8/1976 | France | 239/54 |

Primary Examiner—Barry S. Richman
Attorney, Agent, or Firm—Paul L. Sabatine; Thomas E. Ciotti; Edward L. Mandell

[57] ABSTRACT

A device for dispensing a microcide which consists of a first polymeric material housing a second polymeric material which second material depolymerizes when the device is in the environment of use to form an active microcide. The microcide controls the presence of micro-organisms in the environment over a prolonged period of time.

3 Claims, 2 Drawing Figures

DEVICE FOR DISPENSING MICROCIDE FORMED WHEN DEVICE IS IN ENVIRONMENT OF USE

FIELD OF THE INVENTION

This invention pertains to a dispensing device. More particularly, the invention relates to a device comprising a polymer housing a different polymer that undergoes depolymerization to formaldehyde and is dispersed by the device for controlling the presence of micro-organisms in an environment of use.

DESCRIPTION OF THE PRIOR ART

It has long been recognized that it is highly desirable to control the presence of unwanted micro-organisms in all kinds of environments and to substantially maintain certain articles of manufacture free therefrom. One agent widely used for this purpose is formaldehyde. Formaldehyde is a colorless gas possessing disinfectant and microcidal properties, and it is used as a solution consisting of formaldehyde in water, or it is used in vapor form; see *The Condensed Chemical Dictionary*, 7th edition, by Rose, A., et al, page 429, 1968 published by Reinhold Corporation, New York. While, formaldehyde can be used in these forms, certain disadvantages are associated with their use. For example, when formaldehyde is used as a vapor, the environment or the article needing disinfecting or to be made substantially free of micro-organisms must be tightly sealed to prevent a rapid loss of vapors which inherently defeats obtaining the intended results. Likewise, when formaldehyde is used in solution form, the vapors quickly escape from the solution and make it ineffective for the intended purpose. That is, formaldehyde in these forms is not available only when needed, and these forms are unsuited for the release of formaldehyde at a required time for applying to a preselected environment or article of manufacture for its known effects, see U.S. Pat. No. 4,008,332. U.S. Pat. No. 1,083,561 discloses formaldehyde in solid cake form consisting of formaldehyde, cyanide, naphthalene, petroleum and other ingredients useful as a disinfectant. This form also is unsuited because formaldehyde per se is in the cake which is constantly released as vapors, and also because the cake lacks a means for releasing formaldehyde upon demand in a controlled manner over a required period of time. It will be appreciated by those versed in the subject art in the light of the above presentation that a critical need exists for a device that dispenses formaldehyde when needed at a controlled rate over a required time.

OBJECTS OF THE INVENTION

Accordingly, it is an immediate object of this invention to make available to the art a device that dispenses a microcide and which device overcomes the shortcomings associated with the prior art.

Another object of the invention is to provide a device which contains a polymer that depolymerizes when the device is in use to formaldehyde and is dispensed by the device for controlling the presence of micro-organisms.

Yet another object of the invention is to provide a device for dispensing formaldehyde and which device dispenses formaldehyde upon demand to a preselected environment or article of manufacture.

Still another object of the invention is to provide a device that when externalluy motivated forms in situ a microcide that is dispensed from the device for controlling the presence of micro-organisms.

Other objects and advantages of the present invention, it is believed, will be apparent from the following detailed description of specific embodiments, the drawings and the accompanying claims.

SUMMARY OF THE INVENTION

This invention concerns a dispensing device containing a polymer that is converted to a microcide when the device is in use. The device consists of a first polymer housing a different polymer which latter polymer is converted to the microcide formaldehyde for controlling the presence of micro-organisms in a preselected environment or article of manufacture.

BRIEF DESCRIPTION OF THE DRAWINGS

In the drawings, which are not drawn to scale, but are set forth to illustrate various embodiments of the invention, the figures are as follows.

In the drawings and specification, like parts in related Figures are identified by like numbers. The terms appearing earlier in the specification and in the description of the drawings as well as embodiments thereof, are further described elsewhere in the disclosure.

DETAILED DESCRIPTION OF THE DRAWINGS

Figure 1:
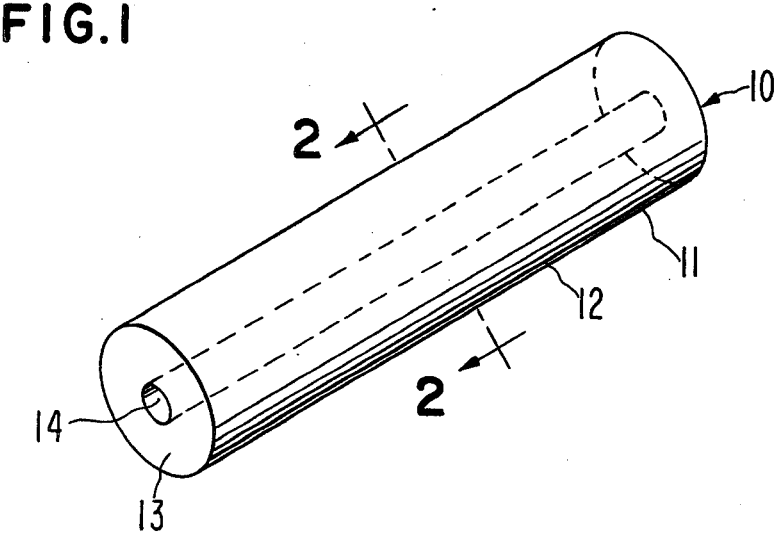
FIG. 1 is a front view of a dispensing device made according to the invention which device produces an active microcide.

Turning now to the drawings in detail, which are an example of a new and useful device for dispensing a microcide and made according to the mode and the manner of the invention, and which example is not to be construed as limiting, one device is indicated in FIG. 1, by the numeral 10. In FIG. 1, device 10 consists essentially of a body 11 shaped, sized and adapted for placement in an environment of use or for disinfecting an article of manufacture. Device 10 has at least one surface 11, or device 10 has a multiplicity of surfaces 12, 13 and 14 for dispensing a microcide from device 10. Body 11 can embrace any preselected geometric shape such as square, round, rectangle, triangle, crescent, circle and the like. Device 10 can be manufactured as a sheet, film, strip, envelope, cylindrical rod, solid matrix, sponge, prism of various cross-section such as cruciform or hexagonal, or the like. In the embodiment illustrated in FIG. 1, device 10 is tubular shaped and it has an internal lumen 14, seen as a dotted line, that extends the length of device 10. Lumen 14 increases the exposed surface area of device 10 for dispensing larger amounts of microcide therefrom. Device 10 optionally is sized to fit the need and it can be from 0.001 micron to 16 centimeters thick or larger, from 1 to 300 millimeters long or larger, and have a cross-section of from 1 to 300 millimeters or larger. In a representative embodiment, device 10 can be a hollow cylinder having a wall thickness of 1.5 cm, a length of 10 cm, and a diameter of 4.5 cm for dispensing microcide to the surrounding atmosphere for a prolonged period of time such as 30 to 40 days or longer.

Figure 2:
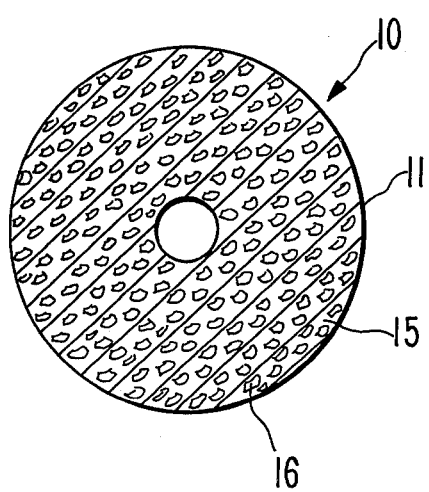
FIG. 2 is a cross-sectional view through 2—2 of FIG. 1 depicting the interior structure of the dispensing device.

Referring to FIG. 2, dispensing device 10 is seen in cross-section along line 2—2 of FIG. 1. As seen in FIG. 2, device 10 comprises a body 11 formed of a first polymer 15 housing a second polymer 16. Polymer 15 is formed of a material that permits the passage of external moisture into polymer 15 and permits passage of polymer 16, depolymerized products and solutions of polymer 16 from polymer 15 to the exterior of device 10. A detailed description of materials and the mode of operation of device 10 appears later in the disclosure.

DETAILED DESCRIPTION OF THE INVENTION

Device 10, used for the purpose of the invention consists of a body 11 formed of a polymeric material 15 that permits the passage of fluid, a different polymer and the depolymerized product of the different polymer and the solutions containing the depolymerized polymer. Representative polymers suitable for forming body 11 include acrylic polymers and copolymers of methacrylate, ethylacrylate, ethylmethacrylate and methylmethacrylate; homopolymers and copolymers of vinyl chloride including vinyl chloride-vinyl acetate copolymer; chlorinated vinyl chloride; polyethylene; polypropylene; ethylene-propylene copolymer; chlorinated polyethylene; ethylene-vinyl acetate copolymer; styrene-butadiene copolymer; acrylonitrite-styrene-butadiene copolymer; polyvinylidene chloride; vinyl chloride-vinylidene chloride copolymers; vinylidene chloride-acrylonitrite copolymer; vinylidene chloride-acrylate ester copolymer; polybutylene terphthalate; vinyl chloride-acrylate ester copolymer; polyamides; polyvinyl acetals such as polyvinyl formal, polyvinyl acetal and polyvinyl butyral; polyethers; polyesters; polyurethanes; chlorosulfonated polyolefins; polyisoprene; polybutadiene, silicone, and the like.

Representative of a polymer 16 used for producing the microcide is paraformaldehyde, which defined as a polymer is a member selected from the group consisting of the cyclic tripolymer of the general formula $(CH_2O)_n$ wherein n is 3, and the linear polymer of the general formula $HO(CH_2O)_mH$ wherein m is 3 to 125. These polymers are white crystalline solids and in the presence of moisture they undergo depolymerization to yield the water soluble microcide and disinfectant formaldehyde; see the *Encyclopedia of Chemical Technology*, by Kirk Othmer, Volume 10, page 81, published by John Wiley & Sons, Inc., New York. In operation, device 10 formed of the first polymer housing the depolymerizable polymer is moisture-activated by fluid entering the first polymer from the surroundings causing (1) the depolymerizable polymer to depolymerize to formaldehyde which as formaldehyde vapors or as a solution containing formaldehyde migrates to the exterior of the device, or (2) the depolymerizable polymers migrate to the exterior of the device and in the presence of moisture is converted to vaporous formaldehyde or a solution containing formaldehyde. In either operation, formaldehyde acts as a microcide or disinfectant to control the presence of micro-organisms. The amount of cyclic or linear polymer housed in the device can vary depending on the need, and it will usually be about 0.001% to 60% by weight based on the weight of the dispensing device. Generally, in the presence of moisture, the cyclic and linear polymers are converted up to 99% formaldehyde, which is released over a prolonged period of time. For devices having low permeability to moisture, the time can be a year or longer.

The expression "controlling the presence of micro-organisms" as used herein means in the general context of this invention, killing, preventing and/or retarding the presence or propagation of micro-organisms in a preselected environment or article of manufacture. The term "environment of use" includes positioning the dispensing device in selected areas of hospital rooms, laboratories, animal quarters, bathrooms, space vehicles, swimming pools, stagnant water, fumigate stored citrus fruits, railroad cars, irrigation canals, animal dips, and the like. In our copending patent application Ser. No. 804,962 filed June 9, 1977 the device is used in combination with patient care apparatus for preventing infection of patients. The present application and our copending application are assigned to the ALZA Corporation of Palo Alto, Calif. The term "article of manufacture" includes germ-free boxes, garment bags, mattresses, pillows and covers, garbage cans, and like articles in need of disinfecting thereof.

The terms microcide and disinfectant as used herein refers to the ability of the formaldehyde dispensed or formed in the environment to kill, cleanse, prevent, and/or retard the presence or propagation of harmful or unwanted micro-organisms as defined supra. The micro-organisms include the fungi *Aspergillus niger, Aspergillus flavus, Rhizopus nigricans, Cladosporium herbarium, Epidermophyton floccosum, Trichophyton mentagrophytes, Histoplasma capsulatum*, and the like. The term micro-organsims also includes antibacterial activity against *Pseudomonas aeruginosa, Escherichia coli, Proteus vulgaris, Staphyloccus aureus Streptococcus faecalis, Klebsiella, Enterobacter aerogenes, Proteus mirabilis*, other gram-negative bacteria, and other gram-positive bacteria, mycobactin and the like. The term also embraces yeast such as *Saccharomyces cerevisiae, Candida Albicans*, and the like. Additionally, spores of micro-organisms, viruses and the like, are within the intent of the invention.

The following examples will serve to further illustrate the present invention, but the invention is not intended to be limited thereto.

EXAMPLE

A dispensing device of tubular shape was made as follows: first, 45 grams of powdered, white solid polymeric paraformaldehyde were blended for 10 to 15 minutes at 35° to 45° C. on a two-roller mill with 55 grams of powdered, transparent ethylene-vinyl acetate copolymer, having a vinyl acetate content of 28% by weight, to produce a film consisting essentially of a homogenous dispersion of depolymerizable paraformaldehyde in the copolymer. Next, the film was ground in a rotary knife grinder to produce particles sized 1/16 to ⅛ inches, averaged size, and the particles then transferred to the hopper of an extruder. Finally, the particles were extruded through a tubing dye at 60° to 70° C. to yield the dispensing device. The device had an outside diameter of 5.2 mm, an inside diameter of 2.2 mm, and a length of 5 cm. The dispensing device exhibited a steady-state delivery of an effective amount of free formaldehyde, when the device was moisture activated, at the rate of 220 μg/hr-cm of device, which level is low enough to prevent micro-organism growth. The rate limiting step for the production of formaldehyde in situ is the chemical reaction consisting of the depolymerization of the polymeric paraformaldehyde to formaldehyde when the device is in use. The devices are stored in dry packages to prevent premature contact with moisture.

It will be understood by those versed in the disinfectant-microcide art, that in the light of the present specification, drawings and the claims, many embodiments of this invention can be made without departing from the scope of the invention. Accordingly, it is to be understood the invention is not to be construed as limited, but it embraces all equivalents inherent herein.

We claim:

1. A device for dispensing para-formaldehyde to an environment of use, the device consisting essentially of:
   (a) a body shaped, sized and adapted for placement in the environment of use, the body formed of a first polymeric material stable in the environment of use and permeable to the passage of moisture and housing a second and different polymer para-formaldehyde;
   (b) a surface exposed to the environment of use defining at least one part of the body formed of said first polymeric material for providing formaldehyde to the enviornment of use; and
   (c) wherein, when the device is in the environment of use, the first polymeric material provides at the surface thereof para-formaldehyde that is converted in the presence of the moisture in the environment of use to formaldehyde, which formaldehyde substantially controls the presence of unwanted microorganisms in the environment of use over prolonged periods of time.

2. A device for dispensing an active microcide to an environment of use, consisting essentially of:
   (a) a shaped body sized and adapted for placement in the environment of use and formed of a first stable polymeric material having a permeability to moisture;
   (b) a reservoir formed of a second polymer, different from said first polymer, that consists essentially of para-formaldehyde which depolymerizes in the first polymer material to the active microcide formaldehyde which is confined in the first polymeric material;
   (c) a surface exposed to the environment defining at least one part of the body formed of said first polymeric material for dispensing the microcide therefrom; and
   (d) wherein the device, when in the environment of use, is moisture activated to dispense microcide by activation resulting from moisture from the environment entering the first polymeric material and contacting the second polymer which thereby depolymerizes in the first polymer, in the presence of said moisture, to the active microcide formaldehyde which is dispensed from the device to the environment of use over a prolonged period of time.

3. The device for dispensing the active microcide according to claim 2 wherein the rate of microcide dispensed from the device is controlled by the rate of depolymerization of the second polymer in the first polymer to the active microcide.

* * * * *